United States Patent [19]
Shalaby et al.

[11] Patent Number: 5,986,050
[45] Date of Patent: Nov. 16, 1999

[54] PERACYLATED PROTEINS AND SYNTHETIC POLYPEPTIDES AND PROCESS FOR MAKING THE SAME

[75] Inventors: Shalaby W. Shalaby, Anderson, S.C.; Jacqueline M. Allan, Bowie, Md.; Joel T. Corbett, Camden, S.C.

[73] Assignee: Poly-Med, Inc., Pendleton, S.C.

[21] Appl. No.: 08/996,366

[22] Filed: Dec. 22, 1997

Related U.S. Application Data

[60] Provisional application No. 60/034,181, Dec. 26, 1996.

[51] Int. Cl.$^6$ .............................. C07K 1/00; A61K 35/78
[52] U.S. Cl. ..................... 530/345; 530/303; 530/342; 530/356; 530/378; 530/402
[58] Field of Search .................................... 530/345, 303, 530/342, 356, 378, 402

[56] References Cited

U.S. PATENT DOCUMENTS

| | | | |
|---|---|---|---|
| 3,764,711 | 10/1973 | Melnychyn et al. | 426/201 |
| 4,045,239 | 8/1977 | Hammer et al. | 106/147 |
| 5,070,188 | 12/1991 | Njieha et al. | 530/324 |
| 5,216,125 | 6/1993 | Kouge | 530/345 |
| 5,260,396 | 11/1993 | Kroner et al. | 527/201 |
| 5,405,766 | 4/1995 | Kallury et al. | 435/174 |
| 5,468,843 | 11/1995 | Boyd et al. | 530/345 |
| 5,523,293 | 6/1996 | Jane et al. | 514/21 |
| 5,677,422 | 10/1997 | Safarian et al. | 530/345 |
| 5,700,904 | 12/1997 | Baker et al. | 530/305 |

OTHER PUBLICATIONS

Gordon et al, *Industrial and Engineering Chemistry*, vol. 38, No. 1, pp. 90–94, 1946.

Gordon et al, Industrial and Engineering Chemistry, vol. 38, No. 12, pp. 1239–1242, 1946.

Hoagland, *Biochemistry*, vol. 7, No. 7, pp. 2542–2546, Jul. 1968.

Hiraki et al, *Chemical Abstracts*, vol. 100, p. 449, Ref. # 22195C (Bull. Chem. Soc. Jpn. 1983, 56(8) 2330–7), 1984.

Ishikawa et al, *J. Jpn. O.l Chem. Soc.* vol. 35, No. 8, pp. 637–642, 1986.

Aitken *Biochem. Soc. Trans.* vol. 17, No. 5, pp. 871–875, 1989.

Gordon, W.G. et al, "Plastic Properties of Higher Fatty Acid Derivatives of Proteins," *Industrial and Engineering Chemistry*, 1946. vol. 38, No. 12, pp. 1243–1245.

Corbett, J.T.et al., "Iontophoretic Controlled Delivery of Modified Insulin," presented at the Fifth World Biomaterials Congress, Toronto, Canada, May 29–Jun. 2, 1996.

Corbett, J.T.et al., "Succinylation of Insulin for Accelerated Ionphoretic Delivery," presented at the Fifth World Biomaterials Congress, Toronto, Canada, May 29–Jun. 2, 1996.

Njieha, F.K. et al., "Modification of Epidermal Growth Factor," *Polymer Preprints*, 1992, vol. 33, No. 3, 536, pp. 233–234.

*Primary Examiner*—Cecilia Tsang
*Assistant Examiner*—Abdel A. Mohamed
*Attorney, Agent, or Firm*—Leigh P. Gregory

[57] ABSTRACT

A method for modifying a protein or polypeptide is disclosed which includes the steps of dispersing a protein or polypeptide in an essentially non-aqueous medium and peracylating the protein or polypeptide with a cyclic anhydride having a carbon chain substituent selected from the group consisting of alkyl and alkenyl groups. Most preferably, the cyclic anhydride is succinic anhydride, although glutaric anhydride may also be employed. Preferably, the step of peracylating the protein or polypeptide is performed in the presence of an acid catalyst, most preferably ρ-toluene sulfonic acid. The resultant modified protein or polypeptide may be employed in numerous applications including drug delivery, absorbable sutures, and thermoplastic films and molded articles.

16 Claims, No Drawings ns: 5,986,050

PERACYLATED PROTEINS AND SYNTHETIC POLYPEPTIDES AND PROCESS FOR MAKING THE SAME

This application claims benefit of Provisional Application 60/034,181 filed Dec. 26, 1996.

1. FIELD OF INVENTION

This invention pertains to surface and bulk modified proteins and synthetic polypeptides with improved properties over their unmodified counterparts. Specifically, this invention describes proteins and synthetic polypeptides acylated with alkyl- and/or alkenyl-succinic and other similarly substituted cyclic anhydrides under practically unhydrous conditions. The peracylated proteins and polypeptides, subject of this invention, may be used as (a) biodegradable film or fiber-formers made by traditional melt-processing; (b) carriers for the controlled delivery of drugs; (c) a prodrug for prolonged bioavailability of the active drug; and (d) water-repellent wool fabric and leather goods.

2. DESCRIPTION OF PRIOR ART

Modification of proteins have long been practiced mostly in the leather, pharmaceutical, and textile industries to achieve certain desirable properties (Carter, 1971; Moncrief, 1975). However, with the exception of a disclosure made by one of the inventors on the acylation of isolated soy protein (ISP) using substituted cyclic anhydrides, all pertinent modifications of the prior art to this invention have been limited to acylation with fatty acids and unsubstituted succinic acid. Typical examples of the pertinent prior art include (a) the acylation of insulin with fatty acid derivatives based on up to 7 carbon atoms and higher acids (Asada et al, 1994; Lindsay et al, U.S. Pat. No. 3,950,517) to increase its stability in the biological environment; (b) acylation of insulin with $C_2$ to $C_{18}$ fatty acid to prolong its biological activity and increase its transcutaneous mobility under iontophoretic conditions (Njieha & Shalaby, 1992a); (c) acylation of insulin with succinic anhydride to increase its transcutaneous mobility under iontophoretic conditions (Corbett et al, 1996); (f) acylation of epidermal growth factor (EGF) with long-chain fatty acids to improve its enzymatic stability (Njieha & Shalaby, 1991, 1992b).

3. SUMMARY OF THE INVENTION

This invention deals with useful derivatives of proteins and synthetic polypeptides, which can be formed by solution, microdispersion, or surface peracylation with alkyl- and alkenyl-substituted anhydrides, such as those of succinic anhydride. Typical examples of derivatives formed by peracylation include those of (a) isolated soy protein (ISP), which are thermoplastic material capable of melt-processing to biodegradable films, rods, and fibers; (b) albumin, which are water insoluble materials for use as drug carriers; (c) casein and zein, which are water insoluble, biodegradable material for use as drug carriers and film formations; and (d) insulin for prolonged control of hyperglycemia. Examples of surface acylated proteins include: (a) surface-treated collagen-based substrates such as sutures for improved in vivo strength retention; (b) leather goods for improved water repellency; and (c) wool and silk fabrics for improved water repellency. Typically, the peracylation is conducted using one or more type of alkyl and/or alkenyl-anhydride in practically non-aqueous medium and, preferably, in the presence of an acidic catalyst. Bioactive proteins and synthetic polypeptides can similarly be modified to prolong their in vivo biological activities.

4. DETAILS OF THE INVENTION

This invention deals with solution microdispersion or surface peracylation of proteins such as isolated soy protein, ricin A-chain, albumin, casein, zein, α-keratin, silk, insulin, epidermal growth factor and collagen as well as synthetic polypeptides, such as somatostatin and LHRH, where each of the acylated heterochain molecules carries at least two alkyl- or alkenyl-succinamide or glutaramide or their corresponding imido species. Sufficient amounts of anhydrides are used to achieve more than two acylations per heterochain molecule (e.g., a protein or synthetic polypeptide chain, peracylated denotes having at least two acyl moieties per heterochain). The acylation results primarily in amide-acid side or terminal groups and can be further cyclized to imide groups upon thermal treatment. Depending on the type of heterochain to be acylated and whether the substrate is fully or partially subjected to the acylation process, outcomes of the acylation can vary. In one instance, the substrate is an ISP and the acylated product differs from the parent molecule in being less hydrophilic, practically water insoluble, and melt-processable. Subsequent melt-extrusion and compression molding of the modified ISP result in fibers and films, respectively. The fibers can be oriented by unidirectional drawing to improve their tensile properties. Similarly, the resulting films can be oriented by constrained, unidirectional or biaxial solid state compression (as described by Shalaby et al, 1996). Both the resulting films and fibers made from acylated ISP are degradable by microorganisms. A typical acylation scheme of ISP is described in Example 1. Molding of typical samples of acylated ISP and properties of the resulting films are given in Example 2.

In a second embodiment of this invention, zein is peracylated with substituted cyclic anhydrides to produce water-insoluble, melt-processable materials for use in the production of biodegradable fibers and films as well as controlled delivery systems of pharmaceuticals and pesticides.

In a third embodiment of this invention, casein is peracylated with substituted cyclic anhydrides to produce melt-processable thermoplastic materials for use in the production of biodegradable fibers, films or carriers for controlled delivery of pharmaceuticals and pesticides.

In a fourth embodiment of this invention, bovine albumin is peracylated to produce practically water insoluble film-forming derivatives, which are biodegradable and can be used as: (a) carriers for the controlled release of traditional organic drugs, pesticides, synthetic peptides, and bioactive proteins; and (b) capsules for oral administration of drugs.

In a fifth embodiment of this invention, insulin molecules are peracylated to (a) reduce their solubility and tendency to dimerize or polymerize; (b) regulate their bioavailability for being in the form of a prodrug; and (c) increase their enzyme stability and, hence, prolong their activity. Growth factors with similar functionalities to insulin can also be acylated to increase their stability against enzymatic degradation and, hence prolong their biological effects. These include fibroblast-derived growth factor (PdGF) and epidermal growth factor (EGF).

In a sixth embodiment of this invention, surface peracylation of silk sutures and fabric or wool fabrics is performed to increase their water repellency and minimize reduction of their tensile strength in a moist environment. Similarly, surface acylation can be used to (a) increase the water repellency of leather goods and improve its frictional properties, and (b) decrease swelling of collagen suture and, hence, maintain its wet strength and improve its tie-down characteristics.

EXAMPLE 1

Peracylation of Isolated Soy Protein

The acid-catalyzed acylation of dry isolated soy protein (ISP) was accomplished in glacial acetic acid using variable amounts of anhydrides. Several acylation experiments were conducted using cyclic anhydride (e.g., 2-octenyl, 2-dodecenyl, and 2-octadecenyl-succinic anhydride), and catalytic amounts of p-toluene sulfonic acid (p-TSA). The acylation was conducted in variable amounts of glacial acetic acid. The acylation charge was heated at 95° C. while mixing for 4 hours. The acylated product was then precipitated by pouring the warm reaction mixture into stirring ice-water. The product was rinsed thoroughly, filtered, and dried under vacuum at 37° C. The dry powder is referred to as SY-P. All SY-P's were characterized by DSC, FTIR, and elemental analysis (in terms of %C and %N) to determine their thermal properties, chemical composition and extent of acylation. Typical acylation reaction charges and elemental analysis data are shown in Tables I and II, respectively.

TABLE I

Typical Acylation Reaction Charges*

| Sample No. | Isolated Soy Protein | OSA | ODSA | DDSA | Anhydride Ratio | Acetic Acid |
|---|---|---|---|---|---|---|
| SY-7 | ISP 620 | 10.0 g | — | — | NA | 40 ml |
| SY-19 | ISP 620 | 7.5 g | 4.15 g | — | 75/25 OSA/ODSA | 47 ml |
| SY-20 | ISP 620 | 7.5 g | — | 9.5 g | 1/1 OSA/DDSA | 45 ml |
| SY-22 | ISP 620 | 6.0 g | 6.7 g | — | 60/40 OSA/ODSA | 51 ml |
| SY-23 | ISP 660 | 10.0 g | — | — | NA | 40 ml |
| SY-24 | ISP 620 | 10.0 g | — | — | NA | 40 ml |
| SY-25 | ISP 660 | 7.5 g | 4.15 g | — | 75/25 OSA/ODSA | 47 ml |

*For all reaction charges noted above, 6.0 g of the indicated soy protein was used. Also, 0.2 g p-toluene sulfonic acid was used in each reaction.
OSA ≡ 2.0 octenyl succinic anhydride
ODSA ≡ 2-octadecenyl succinic anhydride
DDSA ≡ 2-dodecenyl succinic anhydride
All ISP was supplied by Protein Technology International., St. Louis, MO; all anhydrides were supplied by Milliken Corp., Spartanburg, SC.

TABLE II

Typical Elemental Analysis Data

| Protein Derivative | % C* | % N |
|---|---|---|
| SY-7 | 61.43 | 4.69 |
| SY-19 | 61.83 | 4.99 |
| SY-20 | 61.50 | 5.04 |
| SY-22 | 62.66 | 4.84 |
| SY-23 | 60.25 | 5.46 |
| SY-24 | 59.43 | 6.27 |
| SY-25 | 61.87 | 4.97 |

*% C of unmodified ISP = 47.96

EXAMPLE 2

Compression Molding of Peracylated ISP (SY-P) and Film Properties

In a typical molding cycle, SY-P's were converted to 7 to 8 mil. films by compression molding. In a representative system, 3.0 to 3.5 g SY-P was spread evenly in a 5×5 in$^2$ metal frame sandwiched between Teflon-covered molding plates. The molding assembly was heated in a Carver laboratory press at 120 to 180° C. After 5 to 10 min., an eleven metric ton force was applied to the assembly; temperature and load were maintained for 2 to 3 min. The assembly was then quenched to room temperature while under pressure. Films were tested for tensile properties following ASTM D-882-88, "Tensile Properties of Thin Plastic Sheeting." The water vapor transmission rate (WVTR) and oxygen transmission rate (OTR) of the films were obtained using ASTM E 96-80, "Water Vapor Transmission of Materials" and ASTM D3985-81, "Oxygen Gas Transmission Rate through Plastic Film and Sheeting Using a Coulometric Sensor." Film properties are summarized in Tables III, IV, and V.

TABLE III

Tensile Properties of Molded Films

| SY-P | Molding Temperature (° C.) | Tensile Strength (MPa) | % Elongation |
|---|---|---|---|
| SY-7 | 170 | 0.80 ± 0.18 | 17.89 ± 2.08 |
| SY-19 | 170 | 0.30 ± 0.05 | 16.92 ± 1.85 |
| SY-20 | 170 | 0.52 ± 0.26 | 25.01 ± 9.20 |
| SY-24 | 140 | 1.30 ± 0.14 | 14.12 ± 3.25 |
| SY-23 | 140 | 0.89 ± 0.11 | 29.52 ± 5.92 |
| SY-25 | 140 | 1.94 ± 0.21 | 15.99 ± 5.33 |
| SY-7 | 140 | 0.60 ± 0.06 | 30.64 ± 5.34 |
| SY-7 Controls | — | 1.45 ± 0.06 | 14.60 ± 7.31 |
| SY-7 Uniaxial | — | 2.12 ± 0.78 | 32.44 ± 20.04 |
| SY-7 Biaxial | — | 1.68 ± 0.56 | 34.57 ± 16.12 |

TABLE IV

Water Vapor Transmission Rate of Molded Films

| SY-P | Molding Temperature (° C.) | WVTR (g/m$^2$/day) |
|---|---|---|
| SY-7 | 170 | 130 ± 9.90 |
| SY-7 | 140 | 124.7 ± 11.66 |
| SY-7 Biaxial Oriented | — | 78.55 ± 24.11 |
| SY-19 | 170 | 110 ± 13.2 |
| SY-20 | 170 | |
| SY-23 | 140 | 101 ± 17.5 |
| SY-24 | 140 | 90.9 ± 12.0 |
| SY-25 | 140 | 34.64 ± 1.59 |

TABLE V

Oxygen Transmission Rate of Molded Films

| SY-P | Molding Temperature (° C.) | Oxygen (cc/m$^2$/day) |
|---|---|---|
| SY-7 | 170 | 2270 ± 54.77 |
| SY-7 | 140 | 1705 ± 247.5 |
| SY-19 | 170 | 4797 ± 349.6 |
| SY-20 | 170 | 1256 ± 93.70 |
| SY-23 | 140 | 159.3 ± 8.958 |
| SY-24 | 140 | 130.3 ± 3.215 |
| SY-25 | 140 | 2940 ± 130.9 |

The foregoing description of preferred embodiments of the invention has been presented for purposes of illustration and description. It is not intended to be exhaustive or to limit the invention to the precise form disclosed, and modifications and variations are possible in light of the above teachings or may be acquired from practice of the invention. For example, although it is preferred in accordance with the present invention that the essentially non-aqueous medium in which the protein or polypeptide is dispersed is glacial acetic acid, other essentially non-aqueous media are also within the scope of the present invention, such as, for example, propionic acid. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

We claim:

1. A melt-processable soy protein composition made by the process comprising the steps of:

dispersing a soy protein in an essentially non-aqueous medium; and peracylating the soy protein with at least two acyl groups per protein chain by reacting the protein with a cyclic anhydride having a carbon chain substituent comprising at least eight carbon atoms per chain and selected from the group consisting of alkyl and alkenyl groups in the presence of an acid catalyst.

2. The soy protein composition set forth in claim 1 wherein said essentially non-aqueous medium comprises acetic acid.

3. The soy protein composition set forth in claim 1 wherein said essentially non-aqueous medium comprises propionic acid.

4. The protein composition set forth in claim 1 wherein said acid catalyst comprises ρ-toluene sulfonic acid.

5. A melt-processable, synthetic polypeptide composition made by the process comprising the steps of:

dispersing a synthetic polypeptide in an essentially non-aqueous medium; and peracylating the synthetic polypeptide with at least two acyl groups per synthetic polypeptide chain by reacting the synthetic polypeptide with a cyclic anhydride having a carbon chain substituent comprising at least eight carbon atoms per chain and selected from the group consisting of alkyl and alkenyl groups in the presence of an acid catalyst.

6. The synthetic polypeptide composition set forth in claim 5 wherein said essentially non-aqueous medium comprises acetic acid.

7. The synthetic polypeptide composition set forth in claim 5 wherein said essentially non-aqueous medium comprises propionic acid.

8. A method for modifying a soy protein or synthetic polypeptide comprising the steps of:

dispersing a soy protein or synthetic polypeptide in an essentially non-aqueous medium; and peracylating the soy protein or synthetic polypeptide with at least two acyl groups per soy protein or synthetic polypeptide chain by reacting the soy protein or synthetic polypeptide with a cyclic anhydride having a carbon chain substituent comprising at least eight carbon atoms per chain and selected from the group consisting of alkyl and alkenyl groups in the presence of an acid catalyst.

9. The method set forth in claim 8 wherein said cyclic anhydride comprises succinic anhydride.

10. The method set forth in claim 8 wherein said cyclic anhydride comprises glutaric anhydride.

11. The method set forth in claim 8 wherein said acid catalyst comprises ρ-toluene sulfonic acid.

12. A modified, soy protein-based article made by the process comprising the steps of:

forming a soy protein into an article;

subjecting the article to an essentially non-aqueous medium;

surface peracylating the article with a cyclic anhydride having a carbon chain substituent comprising at least eight carbon atoms per chain and selected from the group consisting of alkyl and alkenyl groups in the presence of an acid catalyst.

13. The modified, soy protein-based article set forth in claim 12 wherein said article comprises a suture.

14. The modified, soy protein-based article set forth in claim 12 wherein said article comprises a fabric.

15. The modified, soy protein-based article set forth in claim 12 wherein said cyclic anhydride comprises succinic anhydride.

16. The modified, soy protein-based article set forth in claim 12 wherein said cyclic anhydride comprises glutaric anhydride.

* * * * *